US006393910B1

(12) United States Patent
Korb et al.

(10) Patent No.: US 6,393,910 B1
(45) Date of Patent: May 28, 2002

(54) ONE-PIECE BATTERY CHARGE INDICATOR CAGE

(75) Inventors: Holger M. Korb, Harthausen (DE); Rafal Krupa, Bartlett, IL (US)

(73) Assignee: Illinois Tool Works Inc., Glenview, IL (US)

(*) Notice: Subject to any disclaimer, the term of this patent is extended or adjusted under 35 U.S.C. 154(b) by 0 days.

(21) Appl. No.: 09/491,116

(22) Filed: Jan. 25, 2000

(51) Int. Cl.[7] .............................. G01N 9/18; G01F 23/02
(52) U.S. Cl. .............................................. 73/447; 73/291
(58) Field of Search ............................... 73/291, 290 R, 73/293, 305, 309, 311, 315, 327, 447; 136/290

(56) References Cited

U.S. PATENT DOCUMENTS

| 1,699,633 A | 1/1929 | Sears | |
|---|---|---|---|
| 2,548,558 A | 4/1951 | Raney | |
| 2,631,183 A | 3/1953 | Babis | |
| 3,218,857 A | * 11/1965 | Van Woert | .................... 73/306 |
| 3,597,972 A | 8/1971 | Ryder | |
| 3,597,973 A | 8/1971 | Ryder | |
| 3,893,339 A | 7/1975 | Melone | |
| 3,915,753 A | 10/1975 | Melone | |
| 4,240,282 A | 12/1980 | Nelson | |
| 4,308,817 A | * 1/1982 | Peterson | ...................... 116/215 |
| 4,455,524 A | * 6/1984 | Kendall | ...................... 320/48 |
| 4,866,428 A | 9/1989 | Hinkle | |
| 4,989,453 A | * 2/1991 | Hiiesalu | ...................... 73/440 |

OTHER PUBLICATIONS

Merriam–Webster's Collegiate Dictionary, 10th edition copyright 1998, p. 1152.*

* cited by examiner

Primary Examiner—Hezron Williams
Assistant Examiner—Michael Cygan
(74) Attorney, Agent, or Firm—Pitney, Hardin, Kipp & Szuch LLP

(57) ABSTRACT

The battery charge indicator cage is molded as a single integral piece with two cores coming in and shutting off against each other. The battery charge indicator cage includes an internal diagonal channel in which a colored ball or balls traverse dependent upon the presence of a fluid of at least a predetermined density. A stem is formed within the diagonal channel in order to form the one-ball embodiment. This stem is removed in order to form the two-ball embodiment.

9 Claims, 5 Drawing Sheets

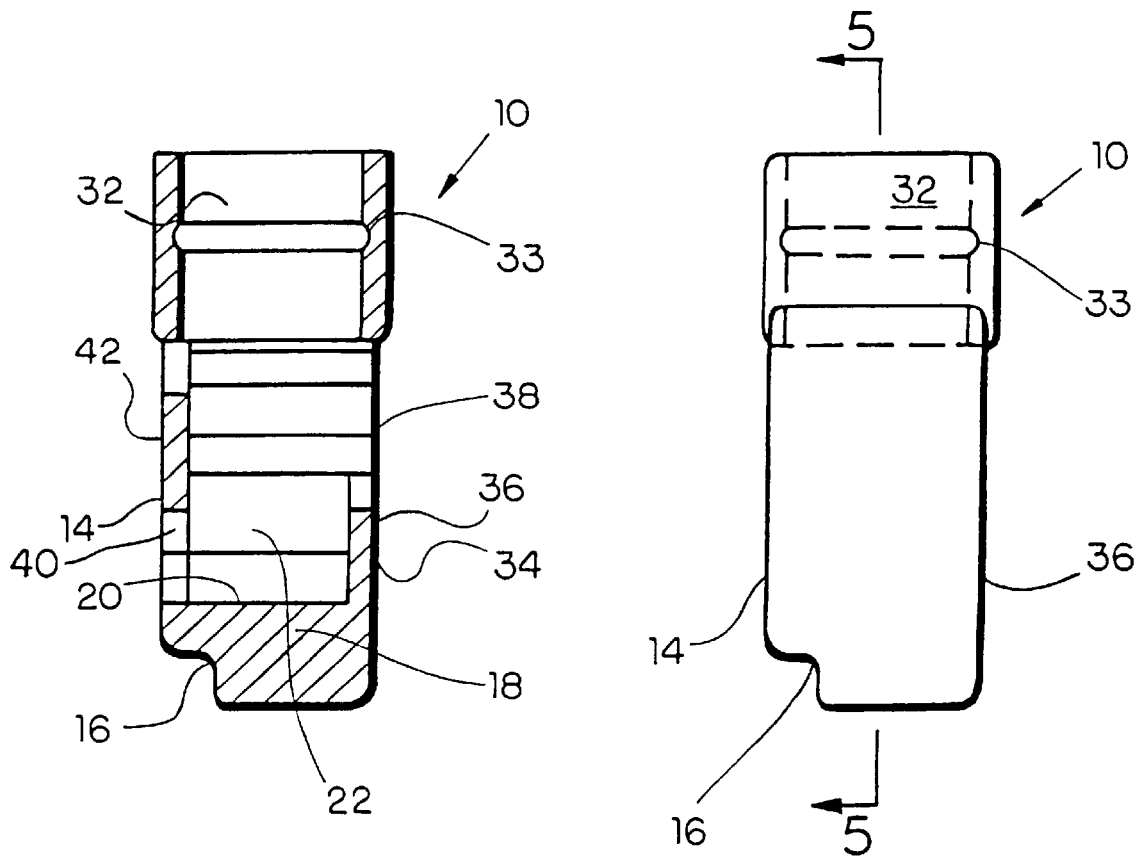
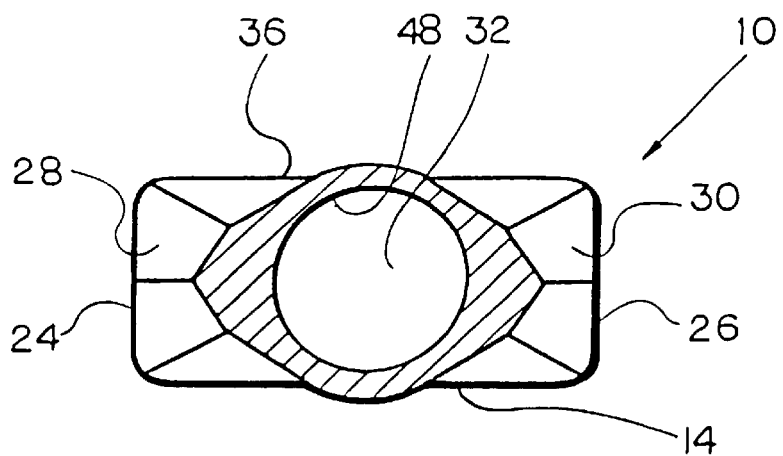
FIG. 3
FIG. 2
FIG. 4

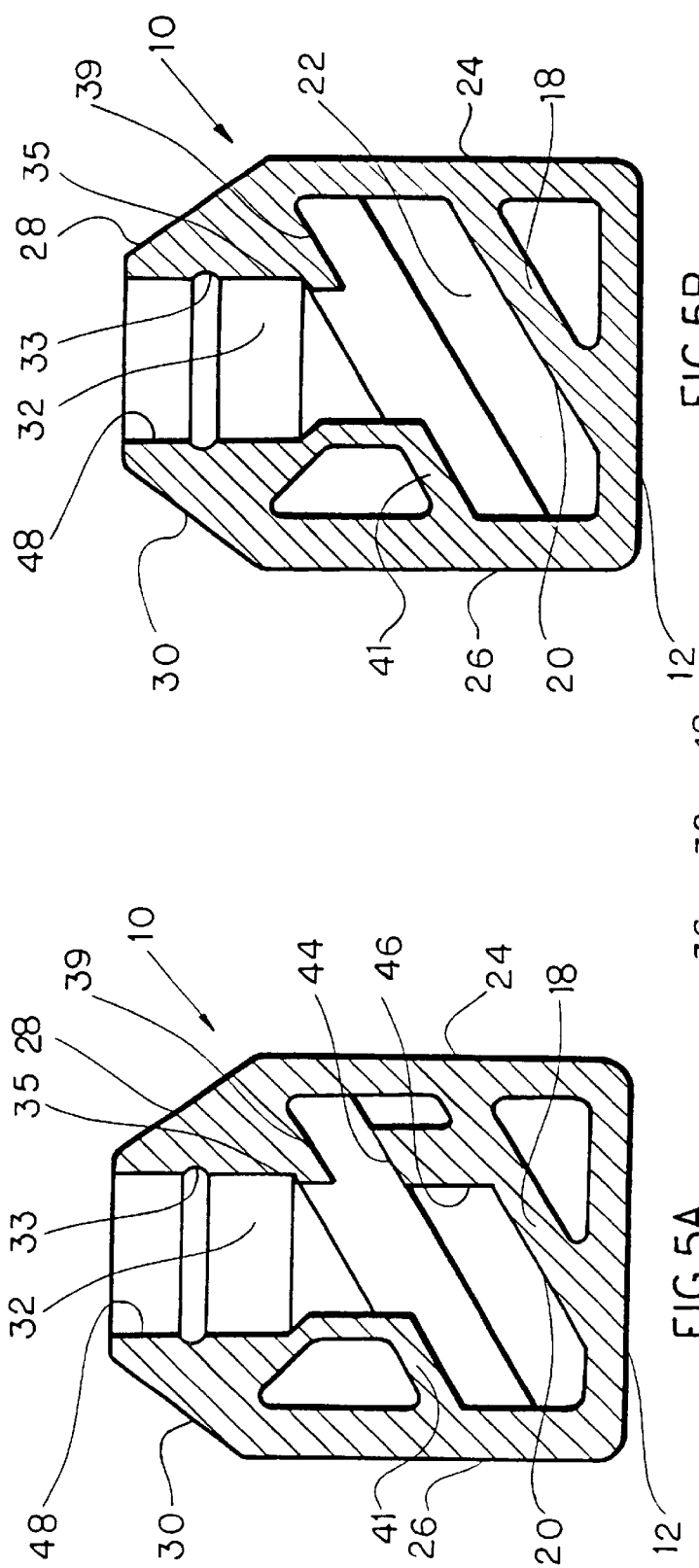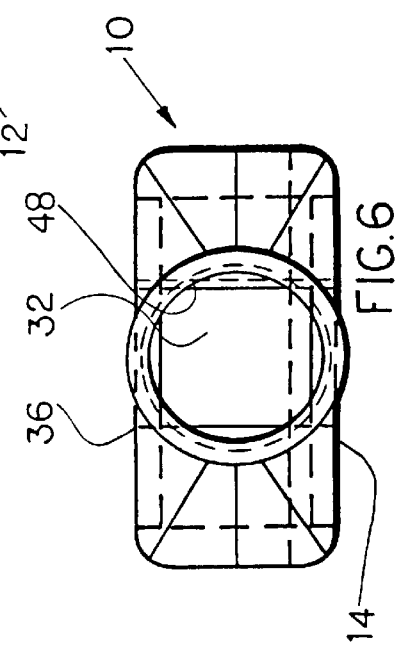

US 6,393,910 B1

ONE-PIECE BATTERY CHARGE INDICATOR CAGE

BACKGROUND OF THE INVENTION

1. Field of the Invention

This invention pertains to a one-piece cage for a battery charge indicator which is used as a hydrometer and liquid level indicator.

2. Description of the Prior Art

In the prior art, it is known to form a cage to enclose and suspend one or more spherical balls within battery fluid in order to monitor both the battery fluid level and the specific gravity of the battery fluid. The cage is typically supported by an elongated transparent rod extending downwardly from the top surface of the battery. Incident light rays are transmitted through the transparent rod and various patterns or colors are transmitted to the viewing surface of the rod on the outer top level of the battery indicating whether or not the rod is immersed in battery fluid and whether or not a ball of a predetermined specific gravity is buoyant within the battery fluid and therefore contacting the transparent rod. Examples of prior art include U.S. Pat. No. 4,886,428 entitled "Remote Battery Cell Specific Gravity and Electrolytic Level Monitor Using Floats and Optical Couplers" issued on Sep. 12, 1989 to Hinkle; U.S. Pat. No. 4,240,282 entitled "Combined Level Indicator and Hydrometer" issued on Dec. 23, 1980 to Nelson; U.S. Pat. No. 3,915,753 entitled "Liquid Indicator for a Storage Battery with a Flame Barrier Vent Filter" issued on Oct. 28, 1975 to Melone; U.S. Pat. No. 3,893,339 entitled "Liquid Level Indicator" issued on Jul. 8, 1975 to Melone; and U.S. Pat. Nos. 3,597,972 and 3,597,973, both entitled "Combined Level Indicator and Hydrometer" and issued on Aug. 10, 1971 to Ryder.

In the prior art, typically these cages have been molded specifically for a one-ball design or for a two-ball design (wherein the balls have different densities to give greater detail in the specific gravity reading). Additionally, these cages have typically been molded as two different pieces which required additional assembly and were typically molded in an open position which required an additional manufacturing step of closing the cage by a cage closer machine. Further adding to the manufacturing and production expense in the prior art has been the difficulty in providing the cage in a consistent orientation to the automated vision inspection system.

OBJECTS AND SUMMARY OF THE INVENTION

It is therefore an object of the present invention to provide a cage for a battery charge indicator which can be adapted for a one-ball or a two-ball design.

It is therefore a further object of the present invention to provide a cage for a battery charge indicator which can be molded as a single integral piece.

It is therefore a still further object of the present invention to provide a cage for a battery charge indicator which is molded in the closed rather than open position in order to eliminate a cage closing step in the manufacturing process.

It is therefore a still further object of the present invention to provide a cage for a battery charge indicator which can be reliably presented in a consistent orientation to a visual inspection system during the manufacturing process.

It is therefore a final object of the present invention to provide a cage for a battery charge indicator which has reduced manufacturing costs.

These and other objects are attained by providing a cage for a battery charge indicator which is molded by two passing cores which come in and shut off against each other resulting in an integral one-piece cage which is molded in the closed position. Additionally, a stem or insert is molded into the cage to provide for a one-ball model cage. This stem or insert prevents the single ball from traveling past the stem tip of the cage support. However, the insert can be removed for the cage to become a two-ball model cage. A notch is molded into a portion of the cage to orient the cage during the assembly process in order to present the cage to the vision inspection system in a consistent position.

BRIEF DESCRIPTION OF THE DRAWINGS

Further objects and advantages of the invention will become apparent from the following description and claims, and from the accompanying drawings, wherein:

FIG. 2 is a side plan view, partially in phantom, of the battery charge indicator cage of the present invention.

FIG. 3 is a cross-sectional view of the battery charge indicator cage of the present invention along plane 3—3 of FIG. 1A.

FIG. 4 is a cross-sectional view of the battery charge indicator cage of the present invention along plane 4—4 of FIG. 1A.

FIG. 5A is a cross-sectional view of the one-ball embodiment of the battery charge indicator cage of the present invention along plane 5—5 of FIG. 2.

FIG. 5B is a cross-sectional view of the two-ball embodiment of the battery charge indicator cage of the present invention along plane 5—5 of FIG. 2.

FIG. 6 is a top plan view, partially in phantom, of the battery charge indicator cage of the present invention.

DETAILED DESCRIPTION OF THE PREFERRED EMBODIMENTS

Figure 1A:
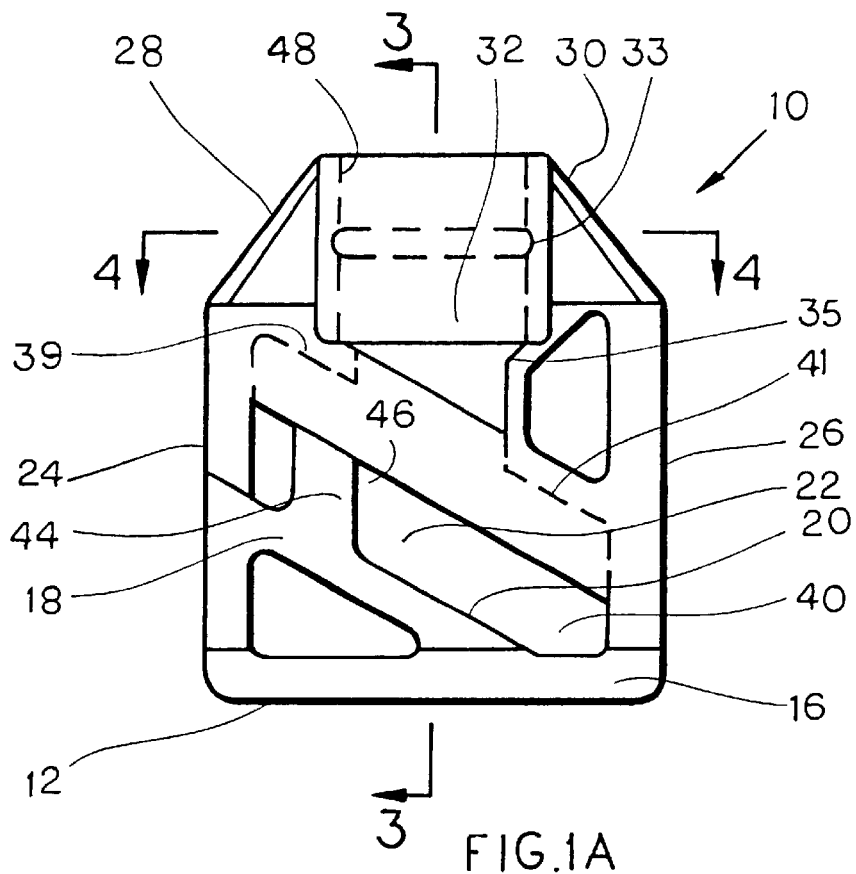
FIG. 1A is a front plan view, partially in phantom, of the battery charge indicator cage of the present invention, showing the stem in place for a one-ball configuration.

Referring now to the drawings in detail wherein like numerals indicate like elements throughout the several views, one sees that FIG. 1A is a front plan view, partially in phantom, of the one-ball embodiment of the battery charge indicator cage 10 of the present invention. Battery charge indicator cage 10 is intended to be a one-piece integral structure of molded plastic. Battery charge indicator cage 10 is intended to be molded with two passing cores which come in and shut off against each other. Base plate 12 forms the bottom of cage 10. As can be seen from FIGS. 2 and 3, base plate 12 includes a lower lateral positioning notch 16 on the front 14 of cage 10 to aid in automated assembly, to provide a uniform element for the automated assembly devices to present cage 10 to the vision inspection system (not shown). Interior diagonal wall 18 rises from base plate 12 to form lower wall 20 of diagonal channel 22 in which, as can be seen from FIGS. 7 and 8, ball or balls 200, 202 traverse.

End walls 24, 26 rise vertically from base plate 12 and, as shown in FIGS. 4 and 6, terminate with upper chamfered surfaces 28, 30, respectively, surrounding mounting aperture 32 which is vertically oriented and is in communication with diagonal channel 22 via oblique throat 35 of somewhat reduced diameter. Circumferential detent groove 33 is formed on cylindrical wall 48 within mounting aperture 32 in order to engage circumferential detent ridge 101 formed upon transparent mounting rod 100 as shown in FIGS. 7 and 8.

Figure 1B:
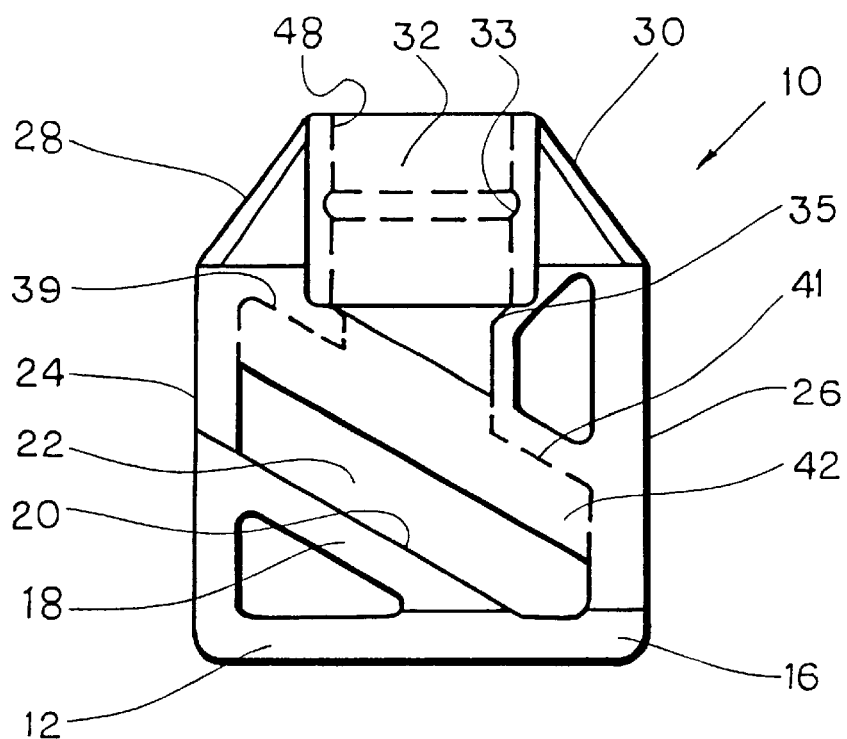
FIG. 1B is a front plan view, partially in phantom, of the battery charge indicator cage of the present invention, showing the stem removed for a two-ball configuration.

As can be seen from FIG. 3, lower diagonal sidewall 34 rises from the rear 36 of cage 10 and terminates below rear diagonal opening 38. Likewise, as can be seen from FIGS. 1A, 1B and 3, front diagonal opening 40 is formed in the front 14 of cage 10 above interior diagonal wall 18 and below upper diagonal sidewall 42. Diagonal channel 22 is limited upwardly by first upper diagonal wall 39 formed inwardly adjacently from end wall 24 and second upper diagonal wall 41 formed inwardly adjacently from end wall 26, with mounting aperture 32 separating first and second upper diagonal walls 39, 41 from each other.

Figure 7:
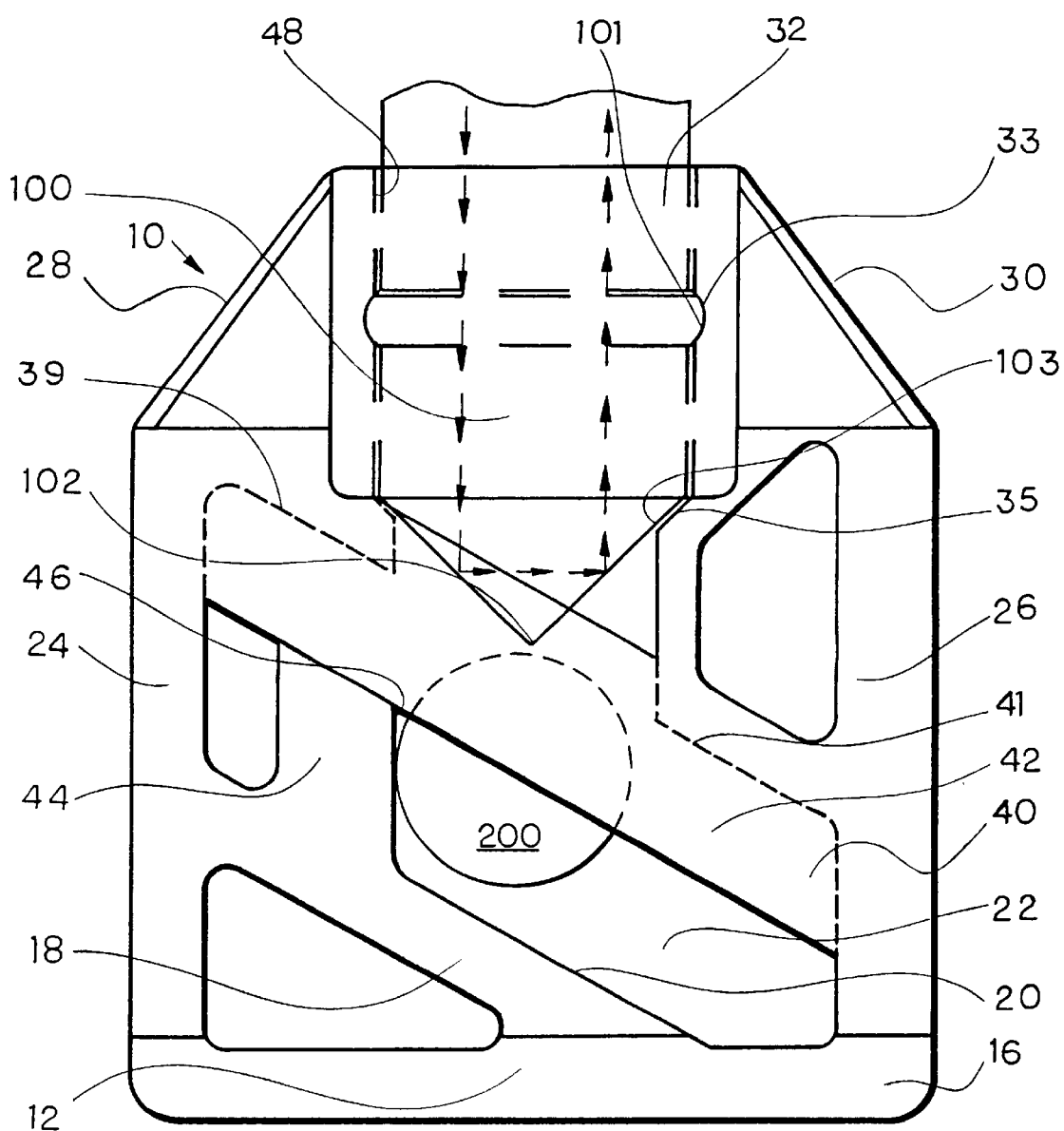
FIG. 7 is a cross-sectional view of the one-ball embodiment of the battery charge indicator cage of the present invention, similar to FIG. 5A, mounted on a transparent rod, showing the single ball in its uppermost position.
Figure 8:
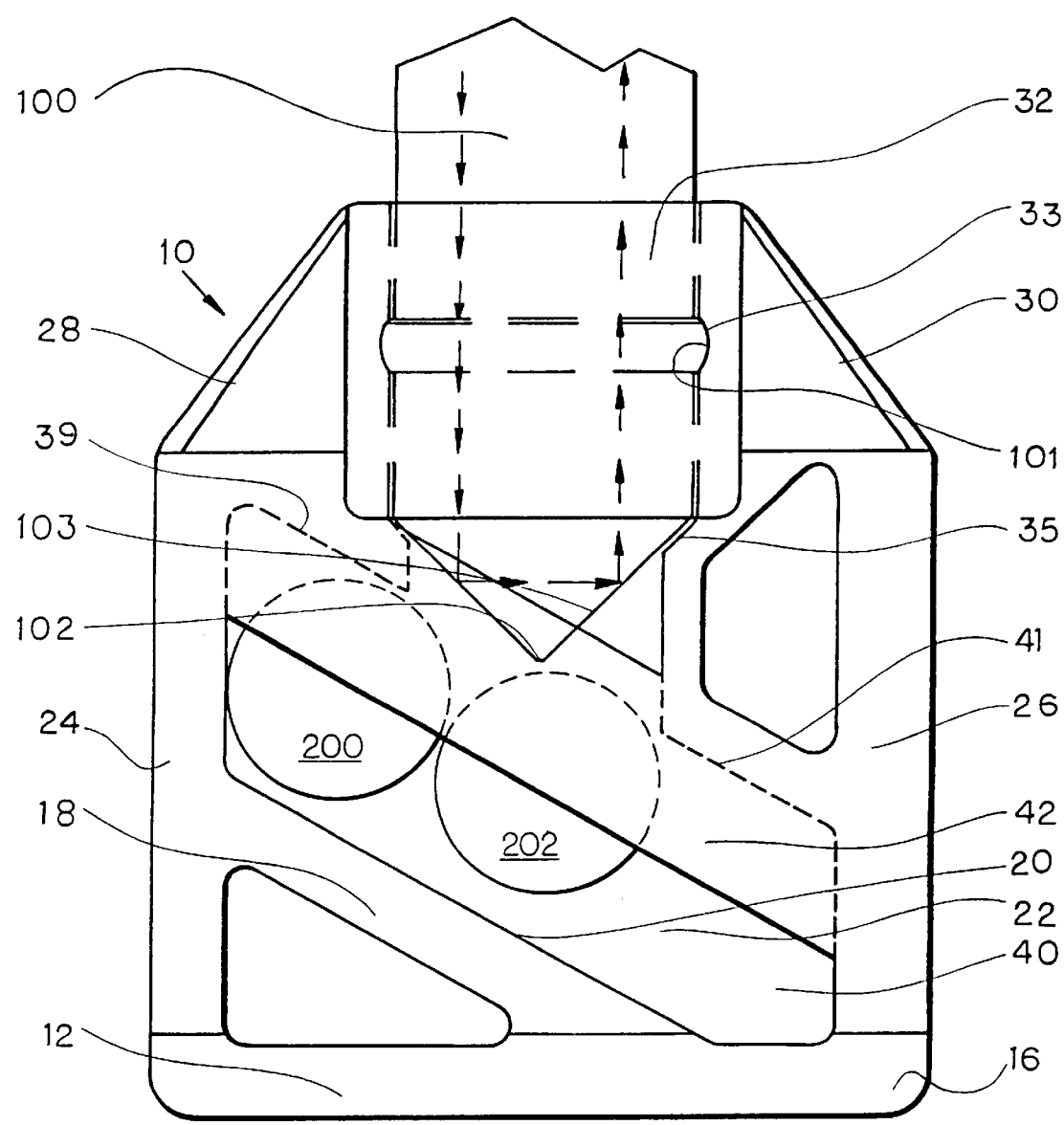
FIG. 8 is a cross-sectional view of the two-ball embodiment of the battery charge indicator cage of the present invention, similar to FIG. 5B, mounted on a transparent rod, showing the two balls in their uppermost positions.

As can be seen from FIGS. 7 and 8, transparent mounting rod 100 is received within mounting aperture 32, circumferential detent groove 33 being engaged by circumferential detent ridge 101. Downwardly pointing ninety-degree tip 102 formed by oblique conical wall 103 extends through mounting aperture 32 and into diagonal channel 22, the insertion of transparent mounting rod 100 being limited by oblique throat 35 engaging oblique conical wall 103.

As can be seen from FIGS. 1A, 5A and 7, in the one-ball embodiment of battery charge indicator cage 10, upwardly extending stem 44 is formed on a relatively upper end of lower wall 20 of diagonal channel 22 with interior wall 46 roughly in line with the interior of oblique throat 35 within aperture 32. However, as can be seen from FIGS. 1B, 5B and 8, stem 44 can be removed or omitted in order to create a two-ball embodiment.

When the liquid level is low, downwardly pointing ninety-degree tip 102 will not be submerged in liquid and a reflective surface will be provided by conical wall 103. Therefore, a bright viewing pattern will appear at an upper end of transparent rod 100 indicating that the liquid level is low. As this upper end of the transparent rod 100 is typically formed on the upper surface of a battery (not shown, this is equally applicable to radiator applications, wherein the radiator fluid level and specific gravity are likewise monitored, the specific gravity of the radiator fluid relating to the freezing point of the fluid), the user is able to ascertain this condition without having to open the battery or otherwise remove any components. When the liquid level is sufficiently high, but the specific gravity is low, then ball or balls 200, 202 are not buoyant within the liquid and sink to a lower point within diagonal channel 22. When the liquid level is sufficiently high, and the specific gravity is sufficiently high (indicating a sufficient concentration of electrolytes), then ball or balls 200, 202 are buoyant and rise within diagonal channel 22 and contact tip 102 as shown in FIGS. 7 and 8. As the balls 200, 202 are of bright colors, such as orange or red (the color of the balls 200, 202 in the two-ball embodiment being different from each other), the bright color of the ball contacting tip 102 or conical wall 103 is transmitted to the viewing surface thereby indicating the state of the fluid being monitored.

To manufacture battery charge indicator cage 10, cage 10 is typically molded as a single integral piece with two passing cores which come in and shut off against each other. Lower lateral positioning notch 16 is used to have the automated assembly device engage cage 10, so that the cage 10 may be presented consistently to automated vision inspection system. Stem 44 is removed if a plurality of balls 200, 202 is desired to be inserted into diagonal channel 22. Ball or balls 200, 202 are inserted into diagonal channel 22 through mounting aperture 32 prior to the insertion and engagement of transparent mounting rod 100 which is joined to the case of the battery (not shown) so that the upper surface of transparent mounting rod 100 provides a visible indicator to the user, while cage 10 is positioned at a level at which is expected to be submerged with a proper fluid level and exposed by an improperly low fluid level.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. A liquid level indicator cage comprising:

a body with two side walls, a front surface, a rear surface, a top surface, and a lower surface;

a diagonal channel formed within said body between said two side walls;

a mounting aperture with a mouth formed on said top surface and extending in communication with said diagonal channel;

said diagonal channel including a detachable member formed at an intermediate location therein and extending inwardly from an interior wall of said diagonal channel, said detachable member confining a single indicator ball of a predetermined density to traversing within a reduced length of said diagonal channel, subsequent detachment and removal of said detachable member lengthening said diagonal channel thereby allowing a plurality of indicator balls of predetermined densities to travel within said diagonal channel.

2. The liquid level indicator cage of claim 1 wherein said single indicator ball and said plurality of indicator balls traverse within said diagonal channel in response to a presence of liquid of a specific gravity greater than said predetermined density or densities.

3. The liquid level indicator cage of claim 2 wherein two side walls, a front surface, a rear surface, a top surface, and a lower surface are molded as a single integral piece.

4. The liquid level indicator cage of claim 3 wherein the cage is formed by two molding cores which shut off against each other.

5. The liquid level indicator cage of claim 3 wherein said lower surface includes a notch for consistent engagement by automated assembly devices.

6. The liquid level indicator cage of claim 5 wherein said mounting aperture includes an oblique throat for positioning of a transparent mounting rod therein.

7. The liquid level indicator cage of claim 6 wherein an interior surface of said detachable member is substantially aligned with an interior diameter of said oblique throat.

8. The liquid level indicator cage of claim 7 wherein said mounting aperture includes an interior circumferential detent groove for engaging a corresponding circumferential detent ridge on the transparent mounting rod.

9. The liquid level indicator cage of claim 8 wherein a first of said front and rear surfaces includes a first diagonal opening to a lower diagonal portion of said diagonal channel, and a second of said front and rear surfaces includes a second diagonal opening to an upper diagonal portion of said diagonal channel.

* * * * *